United States Patent [19]

Pauls et al.

[11] Patent Number: 5,556,990

[45] Date of Patent: Sep. 17, 1996

[54] POLYARYLCARBAMOYLAZA- AND -CARBAMOYLALKANEDIOIC ACIDS

[75] Inventors: Henry W. Pauls, Collegeville; Yong-Mi Choi, Jeffersonville; Robert W. Studt, Reading; Martin P. Maguire, Mont Clare; Alfred P. Spada, Lansdale; Don D. Cha, Eagleville, all of Pa.

[73] Assignee: Rhone-Poulenc Rorer Pharmaceuticals Inc., Collegeville, Pa.

[21] Appl. No.: 357,481

[22] Filed: Dec. 16, 1994

[51] Int. Cl.$^6$ .................... C07D 207/04; C07D 403/08; C07D 417/06; C07D 211/14; C07D 223/02

[52] U.S. Cl. .......... 548/530; 546/174; 546/216; 546/194; 546/198; 546/278.4; 546/278.7; 546/279.1; 546/207; 546/314; 546/270.1; 546/271.7; 546/261; 546/262; 548/170; 540/512; 540/524

[58] Field of Search ................ 548/530, 170; 546/202, 174, 225, 283, 284; 540/512, 524; 514/314, 318, 324, 323, 340, 423, 219

[56] References Cited

FOREIGN PATENT DOCUMENTS

| 0611749A | 8/1994 | European Pat. Off. |
| WO92/15579 | 9/1992 | WIPO . |
| WO93/09115 | 5/1993 | WIPO . |
| WO93/13096 | 7/1993 | WIPO . |
| WO93/21184 | 10/1993 | WIPO . |
| WO93/21183 | 10/1993 | WIPO . |
| WO93/24486 | 12/1993 | WIPO . |
| WO94/03451 | 2/1994 | WIPO . |
| WO94/14805 | 7/1994 | WIPO . |
| WO94/14804 | 7/1994 | WIPO . |

*Primary Examiner*—David B. Springer
*Attorney, Agent, or Firm*—James A. Nicholson; Martin F. Savitzky; Raymond S. Parker, III

[57] ABSTRACT

This invention relates to a class of novel dicarboxy amide derivatives of lipophilic amines which exhibit squalene synthase inhibition properties. More specifically the compounds are bis-aryl and/or heteroaryl alkyl or cycloalkylamino dicarboxy amides. Compounds of this invention reduce levels of serum cholesterol in the body without significantly reducing mevalonic metabolite synthesis. This invention relates also to pharmacological compositions and method of treatment for lowering serum cholesterol levels using the compounds of this invention.

19 Claims, 1 Drawing Sheet

Cholesterol Biosynthetic Pathway

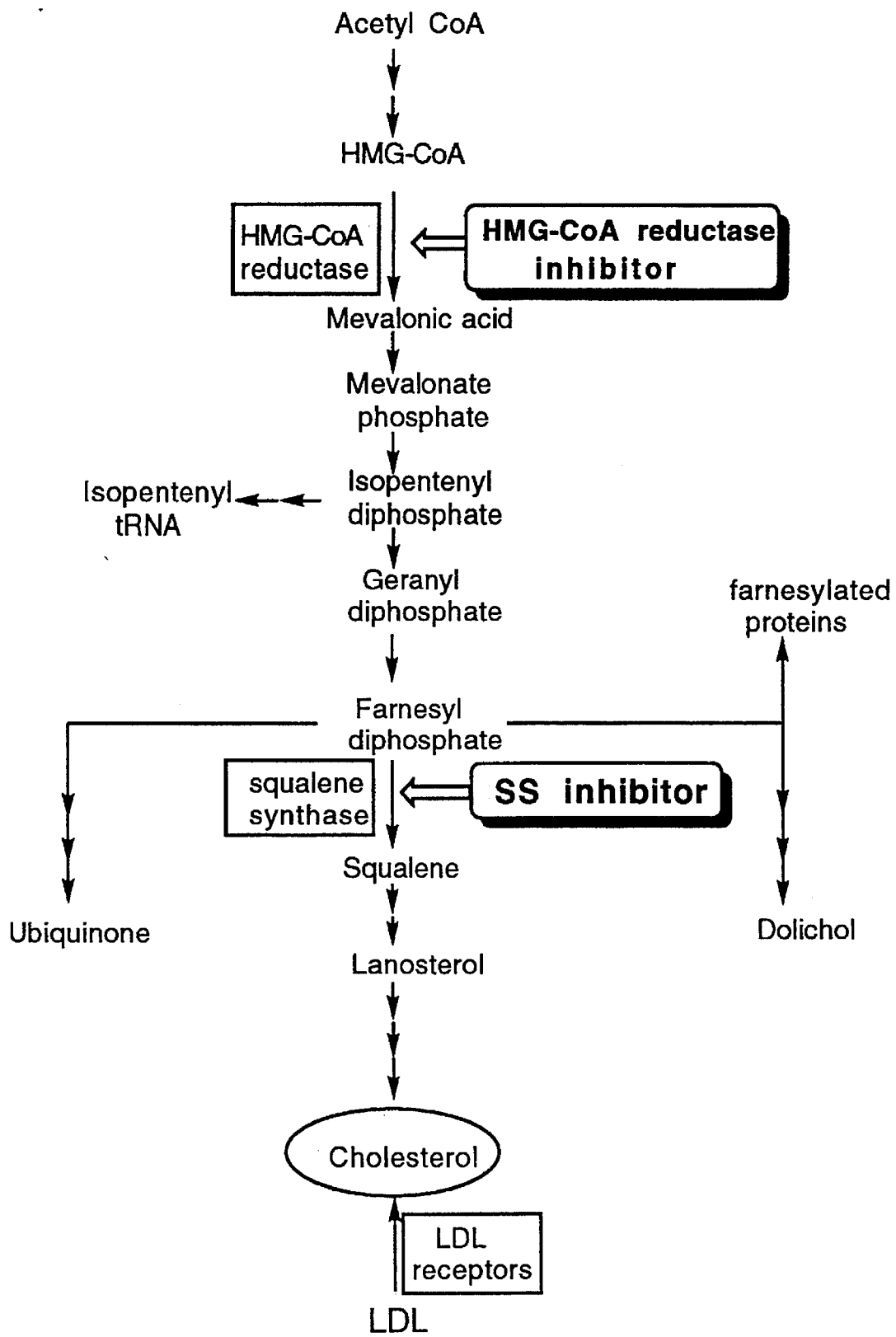
Figure 1  Cholesterol Biosynthetic Pathway

POLYARYLCARBAMOYLAZA- AND -CARBAMOYLALKANEDIOIC ACIDS

FIELD OF THE INVENTION

The present invention relates to a class of novel compounds useful in the treatment of diseases associated with undesirably elevated cholesterol levels in the body, and particularly diseases of the cardiovascular system, such as atherosclerosis. Compounds of the present invention may also be useful in treating fungal infections.

Only about 7% of the total body cholesterol is present in the plasma, where it has been linked to atherosclerosis. The remaining 93% is located in cells, where it performs vital structural and metabolic functions. Excluding the diet, which accounts for approximately one-third of the total body cholesterol, the cells obtain the necessary cholesterol by endogenous biosynthesis (FIG. 1) or by uptake of low density lipoprotein (LDL) from the bloodstream. Various approaches to the control of plasma cholesterol levels have been pursued. However, it has been shown that inhibiting endogenous cholesterol biosynthesis results in uncreased LDL uptake by cells to satisfy their cholesterol requirements. Increased LDL uptake by cells, especially liver cells, has been shown to lower plasma cholesterol levels.

Squalene synthase is a microsomal enzyme that catalyzes the reductive dimerization of two molecules of farnesyl diphosphate to form squalene. While farnesyl diphosphate serves as the precursor to several other biologically important compounds, squalene is utilized only for cholesterol biosynthesis. Consequently, this is the first totally committed step in the biosynthesis of cholesterol (see FIG. 1). Inhibition at this step would stop only de novo cholesterol synthesis while allowing other essential pathways to isopentenyl tRNA, the prenylated proteins, ubiquinone, and dolichol to proceed unimpeded.

Inhibition of HMG-CoA reductase, an enzyme positioned early in the cholesterol biosynthetic pathway, results in a decrease of de novo cholesterol biosynthesis and an accompanying up-regulation of LDL receptors. However due to a large induction in the amount of the HMG-CoA reductase enzyme, the effect of this inhibition is blunted somewhat and the maximum LDL cholesterol reductions attainable are limited. Since inhibition of squalene synthase does not cause the same amount of enzyme induction (HMG-CoA reductase or squalene synthase), its inhibition results in a greater reduction of de novo cholesterol biosynthesis. This translates into more up-regulation of LDL receptors than is seen with an HMG-CoA reductase inhibitor and greater efficacy for lowering circulating LDL levels.

Reported Developments

The literature describes the cholesterol biosynthetic pathway and possible means for the inhibition of squalene synthase. In a series of papers including *J. Am. Chem. Soc.* 104, 7376–7378 (1982) and *J. Am. Chem. Soc.* 111, 3734–3739 (1989), C. Dale Poulter, et al disclose that ammonium substituted cyclopropyl polyene compounds mimic the topological and electrostatic properties of the primary cation and tertiary cation of presqualene diphosphate. and in the presence of phosphate buffer, inhibit squalene synthase. Scott A. Biller et al, *J. Med. Chem.* 31, 1869–1871 (1988), disclose that a series of stable, non-ionizable analogues of farnesyl diphosphate, comprising phosphomethylene phosphate polyene compounds, inhibit squalene synthase.

Paul E. Schurr and Charles E. Day, Lipids, 12, 22–28 (19), describe a compound known as U-41,792, 1-[p-(1-adamantyloxy)phenyl]-piperidine, which is stated to cause a reduction in lower density lipoproteins, and is designated by the authors as having hypobetalipoproteinemia activity International Patent Application published under the Patent Cooperation Treaty having International Publication Number WO 92/15579 is directed to multicyclic tertiary amine polyaromatic squalene synthase inhibitors containing a multiazacyclic ring. U.S. Ser. No. 07/997,818, filed Dec. 29, 1992 is directed to cycloalkyl amine bis-aryl squalene synthase inhibitors. U.S. Ser. No. 08/65,966 is directed to aliphatic amino bis-aryl squalene synthase inhibitors. International patent application No. PCT/US93/12638, filed Dec. 29, 1993, is directed to cycloalkyl amine bisaryl squalene synthase inhibitors. U.S. Ser. No. 08/083,117, filed Jun. 25, 1993, is directed to amino bi- and tri-carboxylic alkane bis-aryl squalene synthase inhibitors. Each of these applications is assigned to the same assignee as the present application.

European Patent Application 94102059.6, filed Feb. 10, 1994 having Publication Number 0611749A1, assigned to Banyu Pharmaceutical Co., Ltd., is directed to substituted amic acid derivatives which are squalene synthase inhibitors.

U.S. Pat. No. 5,135,935 assigned to Merck and Co., is directed to squalene synthase inhibitors which are aryl-oxadiazole-quinuclidines. International Patent Applications published under the Patent Cooperation Treaty having International Publication Numbers: WO 92/12159, 92/12158, 92/12157, 92/12156 92/12160 and 92/15579 and being assigned to Glaxo Group Ltd. and U.S. Pat. Nos. 5,278,320 and 5,258,401, Great Britain Patent 2,275,470A, and European Patent Applications 450,812 A1, 512,865 A2 and 526,936 A2 and being assigned to Merck & co. Inc. are directed to bridged cyclic ketal derivatives for lowering the level of blood plasma cholesterol. Further, PCT patent application having Document Number WO9418157-A1 is directed to viridiofungins which are squalene synthase inhibitors.

Patent Cooperation Treaty Publication Numbers: WO 93/09115 and WO 93/13096, both of which are assigned to Imperial Chemical Industries PLC, and WO 93/21184, WO 93/21183, WO 93/24486, WO 94/03451, WO 94/14803, WO 94/14804 and WO 94/14805, assigned to Zeneca Limited, are all directed to quinuclidinyl-containing squalene synthase inhibitors.

SUMMARY OF THE INVENTION

The present invention is directed to a class of novel polyarylcarbamoylaza and carbamoylalkanedioic acids which exhibit squalene synthase inhibition properties.

More specifically, this invention comprises a class of chemical compounds described as bis-aryl and/or heteroaryl alkyl or cycloalkyl carbamoylaza and carbamoylalkanedioic acids. The compounds of this invention may be described by general formula I.

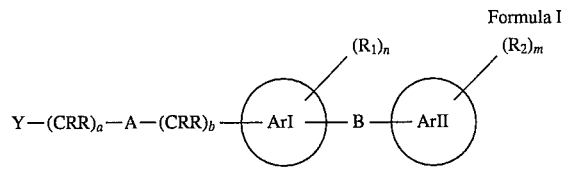

Formula I where:

A is O, S, NR, SO, $SO_2$ or a bond;

B is $(CRR)_{1-2}$, O, S, NR, SO, $SO_2$, RC=CR, C≡C, O=C or a bond;

$$Z \atop R-N-(CRR)_d-CRR-,$$

with ring containing $-CR'$, $(CR''_2)_x$, $(CR''_2)_y$, $N-Z$ ring containing $-CR'$, $(CR''_2)_x$, $(CR''_2)_y$, $C-(CRR)_e-N-Z$, with R on N ring containing $-CR'$, $(CR''_2)_x$, $(CR''_2)_y$, $C-(CRR)_e-N-Z$, with R on N, or $$\text{Alk} \begin{matrix} R \\ | \\ (CRR)_e-N-Z \\ | \\ R'' \\ | \\ R' \end{matrix}$$

$$\begin{matrix} & & COOR \\ & & | \\ O & (CR_3R_4)_f \\ \| & | \\ -C-W-C-R_7 \\ & | \\ & (CR_5R_6)_g \\ & | \\ & COOR \end{matrix}$$

W is a bond, $(CRR)_h$, or NR;

R is independently hydrogen or alkyl;

R' and R" are independently hydrogen, alkyl, alkoxy, hydroxy, halo, haloalkyl or phenyl;

R' and R" together may form a double bond;

$R_1$ and $R_2$ are independently hydrogen, alkyl, alkoxy, hydroxy, halo, haloalkyl or phenyl;

$R_3$, $R_4$, $R_5$ and $R_6$ are independently hydrogen, or alkyl;

$R_7$ is H, NRR or OH and when W is $(CRR)_h$ then $R_7$ is OH;

one of $R_3$, $R_4$, $R_5$, $R_6$ or $R_7$ is OH;

Alk is bi- or tri- carbocycloalkane;

Ar I and Ar II are independently a mono- or di-aryl or heteroaryl;

a and b are independently 0–3;

a+b is 0–4;

d is 0–3;

a+b+d is 1–3;

e is 0–3;

f is 0–2;

g is 0–2;

h is 1–2 m and n are independently 0–2;

x is 1–6;

y is 0–2;

x+y is 3–6; and its stereoisomers, enantiomers, diastereoisomers and racemic mixtures; or a pharmaceutically acceptable salt thereof.

DESCRIPTION OF THE DRAWING

FIG. 1 is a schematic diagram of the biosynthetic pathway of cholesterol.

DETAILED DESCRIPTION AND PREFERRED EMBODIMENTS

As employed above and throughout this disclosure, the following terms, unless otherwise indicated, shall be understood to have the following meanings:

"Aryl" means a monocylic or bicyclic carbocyclic or heterocyclic aromatic ring.

"Mono-aryl or heteroaryl" means a monocylic carbocyclic or heterocyclic aromatic ring. Preferred rings are substituted or unsubstituted pyrrole, thiophene, furan, imidazole, pyrazole, 1,2,4-triazole, pyridine, pyrazine, pyrimidine, pyridazine, thiazole, isothiazole, oxazole, isoxazole, s-triazine and benzene. Preferred groups include phenyl, pyridyl, thienyl, pyridinyl, furyl and pyrimidinyl.

"Di-aryl or heteroaryl" means a bicyclic ring system composed of two fused carbocyclic and/or heterocyclic aromatic rings. Preferred bicyclic rings include substituted and unsubstituted indene, isoindene, benzofuran, dihydrobenzofuran, benzothiophene, indole, 1H-indazole, indoline, azulene, tetrahydroazulene,benzopyrazole, benzoimidazole, benzoxazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benzisoxazine. Preferred groups include naphthyl, benzoxazolyl, indolyl, benzothienyl, benzofuranyl, quinolinyl and benzothiazolyl. "Alkyl" means a saturated aliphatic hydrocarbon, either branched- or straight-chained. Preferred alkyl is "lower alkyl" having about 1 to about 6 carbon atoms. Examples of alkyl include methyl, ethyl, n-propyl, isopropyl, butyl, sec-butyl, t-butyl, amyl and hexyl.

"Aralkyl" means and aryl group bonded to an alkyl group of about 1 to 6 carbon atoms. The preferred "aralkyl" groups are benzyl and phenethyl.

"Alkoxy" means an alkyl-O-group.

"Aryloxy" means an aryl-O-group.

"Halo" means a halogen. Preferred halogens include chloride, bromide and fluoride.

The preferred haloalkyl group is mono, di or trifluoromethyl.

The more preferred compounds of this invention are described by formulae IIa-Vb:

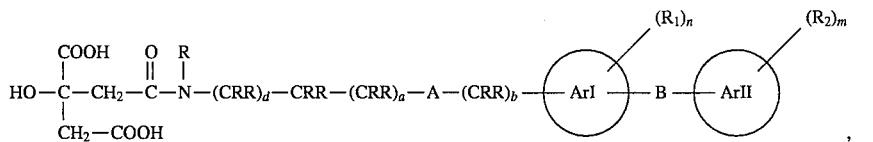
Formula IIa
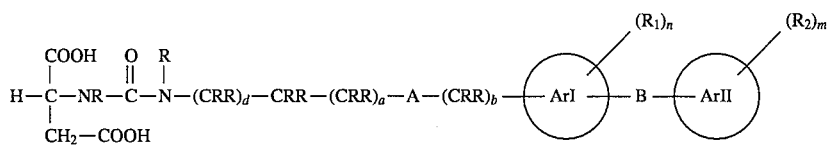
Formula IIb
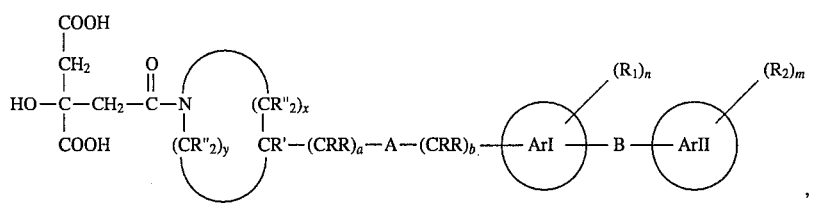
Formula IIIa
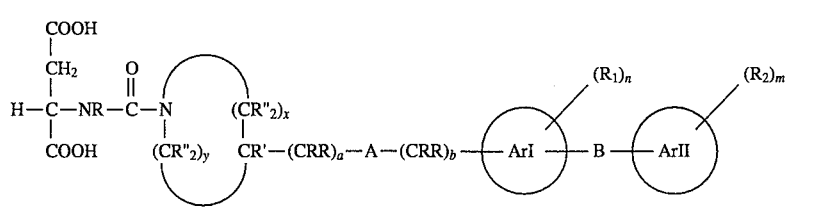
Formula IIIb
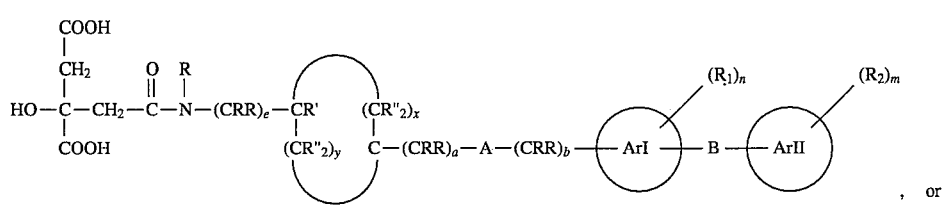
Formula IVa
, or
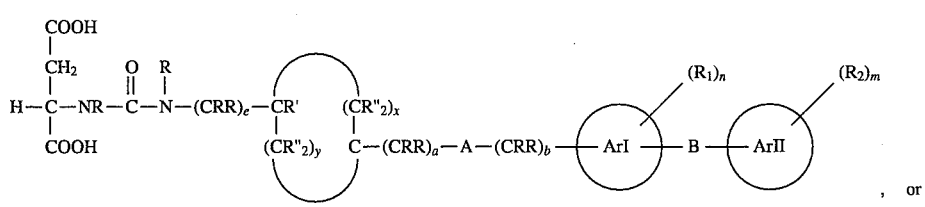
Formula IVb
, or
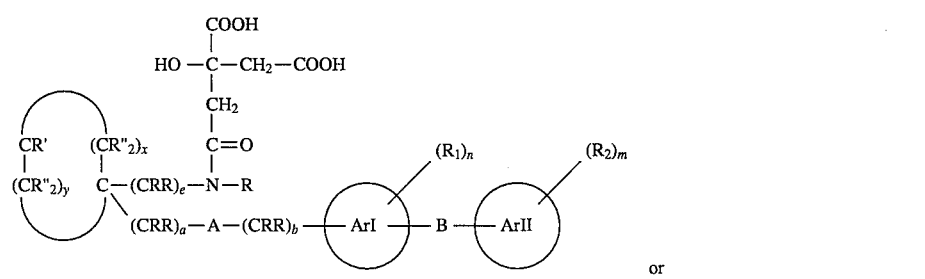
Formula Va
or
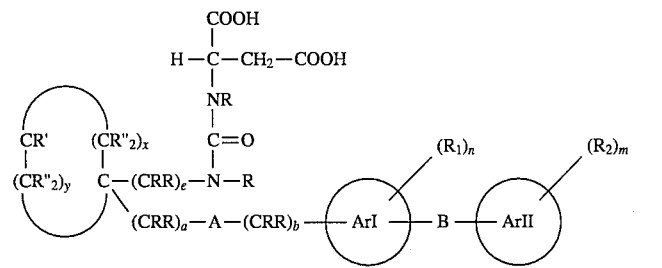
Formula Vb The most preferred compounds of this invention are described by Formulae VI-VIII:

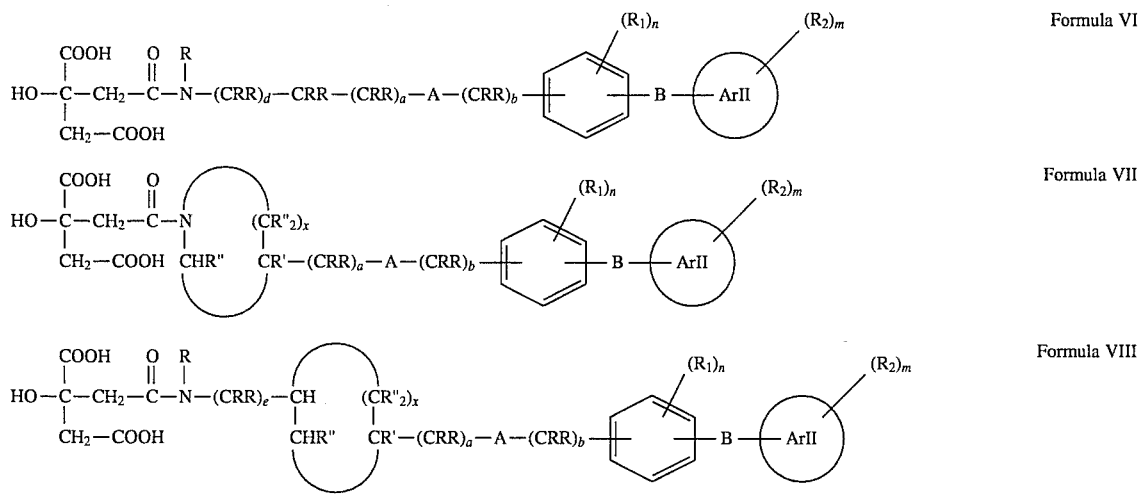

Formula VI

Formula VII

Formula VIII where Ar II is phenyl, naphthyl, quinolinyl, benzoxazoyl or benzthiazolyl.

Of particular importance are compounds described by formulae IX-XIII.

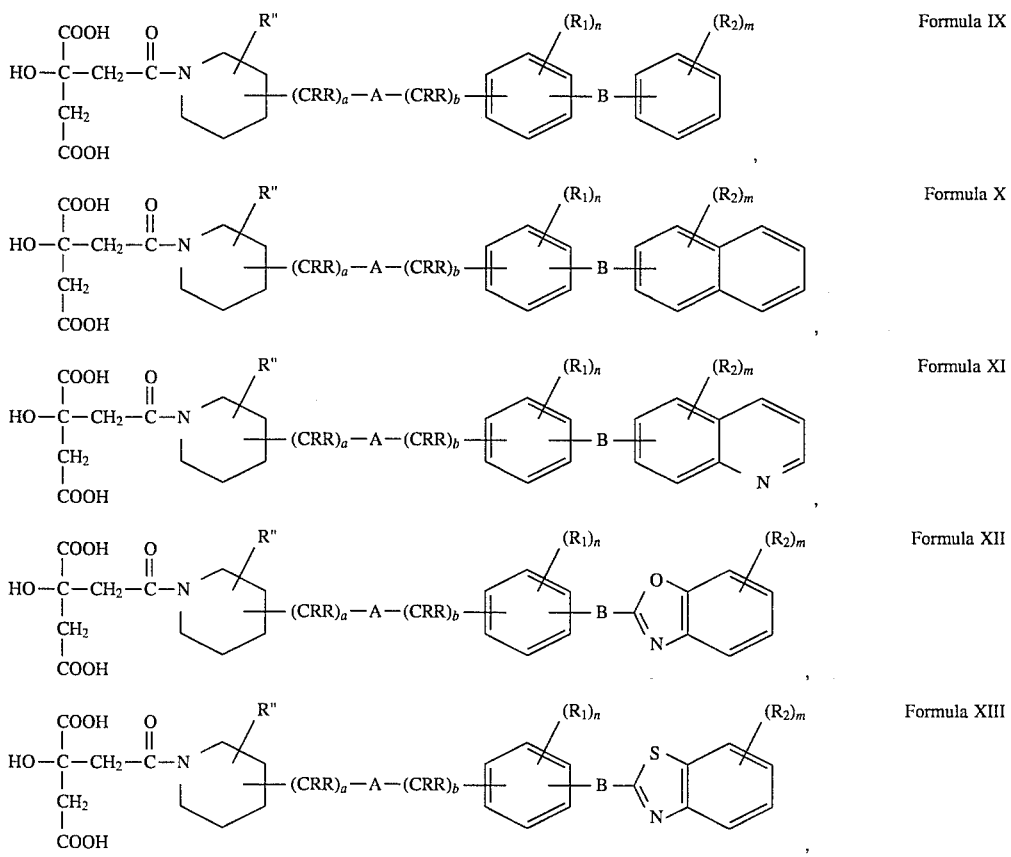

Formula IX

Formula X

Formula XI

Formula XII

Formula XIII

A special embodiment of this invention includes those compounds of Formula XIV:

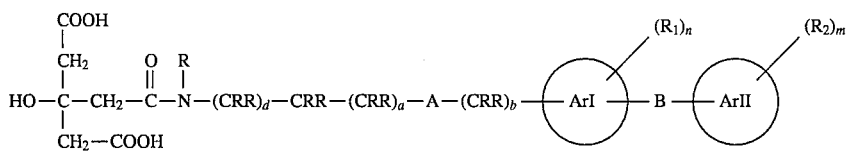

Formula XIV and in particular the compounds of Formula XV:

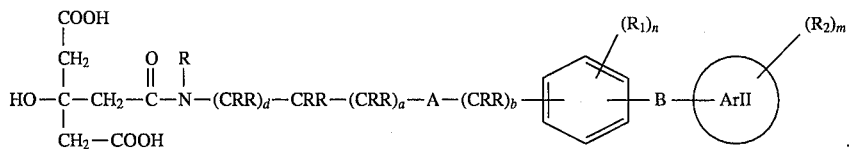

Formula XV

The compounds of the present invention may be prepared by the following general methods.

Step A1

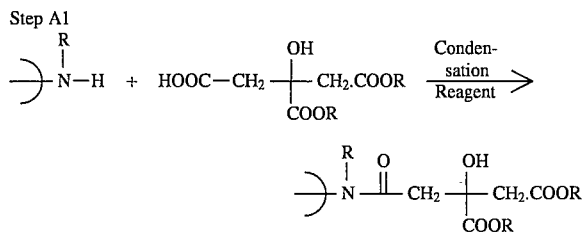

Step A2

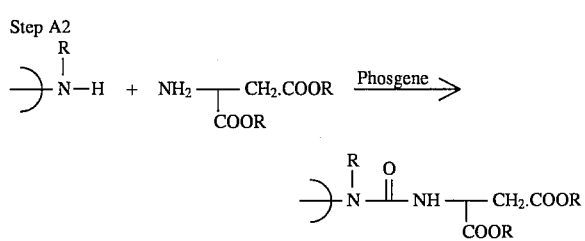

Step B1

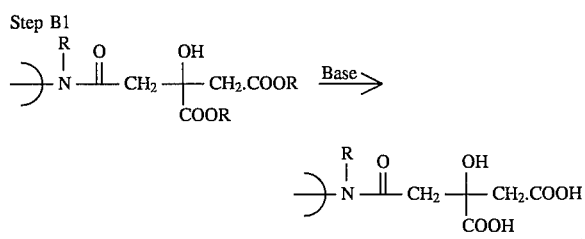

Step B2

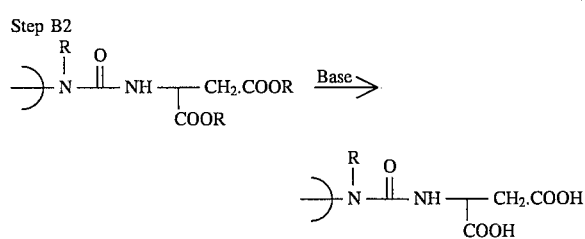

In general the first step (A1) involves coupling of a dialkyl citrate with a lipophilic amine in the presence of a condensation reagent like those described for the synthesis of amide bonds. The primary or secondary amine starting material are in some cases commercially available but more often are prepared by methods described herein or in copending application Ser. Nos. 08/065,966, 083,117 and PCT/US93/12638. The dialkylcitrates are prepared from the citrate triesters by treatment with one equivalent of a strong base followed by chromatographic isolation of the monoacid.

The dicarboxybutanoyl derivatives can be prepared by treating a starting amine with one equivalent of the dialkyl citric acid such as 1-(3-dimethylaminopropyl) 3-ethylcarbodiimide hydrochloride (EDC), 0.5–1.0 equivalent of hydroxybenztriazole (HOBT) and two equivalents of a tertiary amine like triethyl amine in a polar aprotic solvent preferably tetrahydrofuran (THF) at room temperature under argon overnight. The reaction is worked up by any one of a number of standard extractive methods. For example, the reaction mixture is concentrated to dryness and diluted with a polar solvent such as methylene chloride. A basic extractive workup followed by flash chromatography provides the pure product. Alternatively the reaction mixture is diluted with ethyl acetate washed successively with dil. hydrochloric acid and sat. bicarbonate then chromatographed as above.

The dicarboxylic acids are generally obtained from the diethyl esters by standard hydrolysis conditions as shown in Step B 1. A solution of the diester in ethanol or ethanol/THF is treated with a strong inorganic base such as 10N sodium hydroxide, preferably three-four molar equivalents, at room temperature under argon overnight. (If after several hours a precipitate forms, a few milliliters of water is added to the reaction mixture until the solution is homogeneous again). After stirring a total of 24–48 hours, a precipitate may form. In such a case the reaction mixture may be further concentrated and the solid collected and washed with cold ethanol and/or diethyl ether and the product isolated as the disodium salt.

Alternatively, the solid may be dissolved in water and acidified to pH<4. If a solid is formed, it is filtered and washed several times with water then dried under vacuum to yield the free diacid. The product may be further purified if necessary using high pressure liquid chromatography (HPLC). If the free acid is water soluble, the aqueous solution is concentrated and the product is isolated by HPLC.

In general, the ureas can be prepared by standard coupling methods as shown in Step A2. A solution of the amine in an organic solvent preferably methylene chloride ($CH_2Cl_2$) is treated with phosgene or its equivalent, preferably triphosgene (⅓ equivalents) and excess tertiary amine, preferably 3.5 fold excess of triethylamine, at room temperature under argon for several hours, preferably five hours. The reaction mixture is subsequently treated with one equivalent of 2-aminobutandioic acid dimethyl ester. If a hydrochloride salt is used a slight excess of tertiary amine, preferably 1.1 fold excess of triethylamine is added. The reaction mixture is heated to 30°–40° C. preferably 40° C. overnight. An extractive workup followed by flash chromatography yields the product.

The urea derivatives are generally obtained by treating the diester (step B2) with an excess of a strong inorganic base such as lithium hydroxide hydrate preferably ten equivalents in THF/methanol/water (3:1:1 v/v/v) at room temperature overnight. The reaction mixture is evaporated to near dryness then dissolved in hot water. The aqueous solution is washed with an organic solvent such as diethyl ether then acidified with concentrated HCl until the pH is ca. 1–3, but preferably 2. Upon precipitation of a white solid the suspension is placed in the refrigerator for about 30 min. The solid is collected and then dried on the vacuum pump. If no product precipitates the water is removed under vacuum and the product is isolated by HPLC.

Certain compounds of this invention may have at least one asymmetric carbon atom. Further, certain compounds of this invention may exist in their cis or trans configuration. As a result, those compounds of this invention may be obtained either as racemic mixtures, diastereoisomeric mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity. In general, the compounds of this invention are prepared as mixtures of steroisomers, containing less than the maximum number of stereoisomers for a given number of sterocenters.

Reference to the separation of cis and trans isomers by chromatography may be found in W. K. Chan, et al, *J. Am. Chem. Soc.* 96, 3642 (1974).

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds*: Optical Resolution Information Center, Manhattan College, Riverdale, N.Y. Such procedures are useful in the practice of this invention. A further useful reference is Enantiomers, *Racemates and Resolutions*: Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, oxalic, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "*Protective Groups in Organic Synthesis*" by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

Since the compounds of this invention have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to the skilled artisan. This would further be dependent on the ring involved.

The starting amines, reagents and the protected citrate (3-Hydroxy-3,4-bis(ethoxycarbonyl)butanoic acid) used for the preparation of the compounds of the present invention may be obtained by the following representative preparations.

Preparation 1

3-Hydroxy-3,4-bis(ethoxycarbonyl)butanoic acid

A solution of triethyl citrate (34.1 g, 123 mmol) in ethanol and water (30 ml) is treated with sodium hydroxide (3.70 g, 92.6 mmol) and stirred at room temperature under argon for 4.5 hours. The reaction mixture is concentrated on a rotary evaporator then diluted with water (50 ml). The pH is adjusted to ca. 1 using 2N HCl. The aqueous solution is then extracted with a large excess of chloroform (4×150 ml). The combined organic layers are dried (MgSO$_4$), filtered and concentrated to give crude oil. Purification by flash chromatography (5% MeOH/CH$_2$Cl$_2$ to 1% AcOH/5%MeOH/CH$_2$Cl$_2$) gives 8.72 g of product (38% as a racemate.

$^1$H NMr (300 MHz, CDCl$_3$)δ 1.26 (t, 3H, J=9 Hz), 1.31 (t, 3H, J=3 Hz), 2.88 (m, 4H), 4.16 (q, 2H, J=2 Hz), 4.30 (q, 2H,

Preparation 2

3-[4-(Benzoxazol-2-yl)benzyloxy]piperidine

3-Hydroxypiperidine hydrochloride (2.5 g, 18.2 mmol) is treated with di-tert-butyldicarbonate (4.16 g, 19.06 mmol) and 4-methylmorpholine (4.2 ml, 38.2 mmol) in anhydrous methylene chloride (50 ml) overnight at room temperature.

The reaction mixture is diluted with methylene chloride (250 ml) and washed with 5% hydrochloric acid and saturated bicarbonate solution. The organic layer is dried ($Na_2SO_4$) and concentrated and used without further purification.

A portion of N-tert-butoxycarbonyl-3-hydroxypiperidine (0.923 g, 4.6 mmol) so obtained is dissolved in anhydrous tetrahydrofuran (75 ml) and treated with sodium hydride (0.275 g, 60%, 6.88 mmol), previously washed with anhydrous hexane (2 X). The resulting suspension is stirred at room temperature for one hour then treated with 4-(benzoxazol-2-yl)benzyl bromide (1.32 g, 4.6 mmol) and a catalytic amount of tetrabutyl ammonium bromide (0.05 g). Stirring is continued for 20 hours at room temperature and the reaction is quenched with aqueous ammonium chloride. The reaction mixture is diluted with methylene chloride (250 ml) and separated. The aqueous layer is washed with ethyl acetate; the organics are combined and concentrated. The residue is chromatographed (20% ethyl acetate/hexane) to give the intermediate carbamate (1.0 g).

A portion of the carbamate (0.52 g, 1.27 mmol) is dissolved in a solution of 10% trifluoroacetic acid in anhydrous methylene chloride (10 ml). The solution is stirred overnight at room temperature, diluted with ether and concentrated to about 15 ml. The solid that precipitated is collected as the trifluroacetate salt of the title compound (0.50 g, 51% two steps).

MS (El+ion) m/z 408 $M^+$ $^1$H NMR ($CDCl_3$, 300 MHz): δ 1.7–2.0 (m, 3H), 2.03–2.20 (m, 1H), 3.2 (m, 3H), 3.25 (m, 1H), 3.7 (m, 1H), 4.65 (s, 2H), 7.35 (m, 2H), 7.5 (d, 2H, J=7.9 Hz) 7.58 (m, 1H), 7.77 (m, 1H), 8.25 (d, 2H).

In a like manner by the methods described in preparation 2 the following amines are prepared:

Preparation 3

3-[4-(Benzoxazol-2-yl) benzyloxymethyl]piperidine $^1$H NMR (300 MHz, $CDCl_3$)δ 1.19 (1 H, m), 1.68 (1 H, m), 1.63–1.65 (4 H, m), 2.41 (1 H, m), 2.58 (1 H, m), 3.01 (1 H, m), 3.19 (1 H, m), 3.36 (2 H, m), 4.57 (2H, s), 7.36 (2 H, m), 7.48 (2 H, d, J=8.1 Hz), 7.59 (1 H, m), 7.78 (1 H, m), 8.24 (2 H, d J=8.1 Hz).

Anal. calcd. for $C_{20}H_{22}N_2O_2 \cdot 1.00H_2O$: C, 70.57; H, 7.11; N, 8.23. Found: C, 70.60; H, 6.58; N, 8.23.

Preparation 4

3[4-(Benzoxazol-2-yl)benzyloxy]pyrrolidine $^1$H NMR (300 MHz, $CDCl_3$)δ 1.93 (3 H, m), 2.88 (2 H, m), 3.12 (2 H, m), 4.15 (1 H, m), 4.56 (2 H, br s), 7.36 (2 H, m), 7.50 (2 H, d, J=8.1 Hz), 7.59 (1 H, m), 7.78 (1 H, m), 8.24 (2 H, br d, J=8.1 Hz).

Anal. calcd. for $C_{18}H_{18}N_2O_2 \cdot 0.55H_2O$: C, 71.05; H, 6.33; N, 9.21. Found: C, 71.03; H, 6.25; N, 9.07.

Preparation 5

2-(S)-[4-(Benzoxazol-2-yl)benzyloxymethyl]pyrrolidine

A solution of 3.00 g (18.1 mmol) of L-proline methyl ester hydrochloride, 5.05 g (18.1 mmol) of trityl chloride and 10 mL of triethylamine in 40 mL of 1,2-dichloroethane is stirred at 22° C. After a few minutes, a thick precipitate began to form. An additional 20 mL of 1,2-dichloroethane is added and the mixture is heated to 60° C. and stirred for 3 hrs. The reaction mixture is partitioned between water (100 mL) and $CH_2Cl_2$ (100 mL). The organic layer is washed with satd. $NaHCO_3$ (50 mL), dried ($MgSO_4$) and evaporated. The residue is recrystallized from hexane/EtOAc to give 5.76 g of 1-trityl-pyrrolidine-2-carboxylic acid, methyl ester as a white crystalline solid which is used directly in the next step.

A solution of 5.00 g (13.4 mmol) of the above ester in 50 mL of diethyl ether is added dropwise to a mixture of 0.509 g (13.4 mmol) of solid lithium aluminum hydride in 10 mL of ether while stirring under nitrogen. The mixture is brought to a gentle reflux and an additional 6.7 mL (6.7 mmol) of a 1M solution of lithium aluminum hydride in ether is injected by syringe. After refluxing for 2 hrs the reaction is cooled to 22° C. and quenched with 10 mL of methanol. The mixture is partitioned between 100 mL of 0.5M NaOH and 50 mL of ether and then stirred vigorously for 25 minutes and filtered. The ether layer is separated, washed with brine (30 mL), dried ($MgSO_4$) and evaporated to give 4.20 g of (1-tritylpyrrolidin-2-yl)methanol as a white foam. By the method described in preparation 2, this material is used to prepare the title compound which is recrystallized from ethyl acetate/hexane.

$^1$H NMR (300 MHz, free base, $CDCl_3$)δ 1.79 (1 H, m), 2.01 (3 H, m), 3.22 (2 H, t, J=7.1 Hz), 3.67 (2 H, m), 3.81 (1 H, m), 5.56 (1 h, d, J=12.4 Hz), 5.61 (1H, d, J=12.4 Hz), 7.33 (2 H, m), 7.44 (2 H, d, J=8.3 Hz), 7.56 (1 H, m), 7.75 (1H, m), 8.18 (2 H, d, J=8.3 Hz), 9.10 (1 H, br s). Anal. calcd. for $C_{19}H_{20}N_2O_2 \cdot HCl$: C, 66.18; H, 6.14; N, 8.12. Found: C, 66.32; H, 6.18; N, 8.02.

Preparation 6

6-α-(4-Styrylphenyl)cyclohex-4-enyl-β-amine

4-Stilbenecarboxyaldehyde (10.4 g, 0.05 mol), β-alanine (0.44 g, 0.005 mmol), nitromethane (4.6 g, 0.075 mmol) and ethanol are combined and heated to reflux for 10 hours. The reaction mixture is filtered and the yellow solid recrystallized from ethanol to give the 4-(2-nitrovinyl)stilbene (9.2 g, 73%). Anal. Calc. for $C_{31}H_{35}NO_7 \cdot 0.425 H_2O$: C 76.49, H 5.18, N 5.58 Found: C 75.89, H 5.27, N 5.94.

The intermediate 4-(2-nitrovinyl)stilbene (5 g, 19.9 mmol) and excess butadiene in toluene (12 ml) is heated to 140° C. for 20 hrs in a sealed tube. The yellow solid which formed upon cooling is filtered and recrystallized from ethanol to give 3.38 g of 2-α-Nitro-1-β-(4-styrylphenyl)cyclohex-4-ene (56%).

MS (El+ion) m/z 305 $M^+$

Anal. Calc. for $C_{31}H_{35}NO_7 \cdot 0.425 H_2O$: C 78.66, H 6.27, N 4.59 Found: C 78.22, H 6.38, N 4.46.

Nickel (11) acetate tetrahydrate (1.91 g, 7.6 mmol) in water (77 ml) is treated in two portions with a solution of sodium borohydride (0.579 g, 15.0 mmol) in 0.1M aqueous NaOH. After the evolution of gas had ceased the granular suspension is centrifuged and the supernatent liquid decanted. The nickel boride is washed with distilled water and again centrifuged to remove the washings. This process is repeated twice more using water then washed with ethanol and finally isopropanol.

A portion of the nickel boride (1.75 g, mmol) is added to 2-α-nitro-1-β-(4-styrylphenyl)cyclohex-4-ene (0.9 g, 2.97 mmol), in isopropanol (60 ml) under argon. The mixture is heated to reflux and treated with hydrazine hydrate (0.66 g, 13.4 mmol) in isopropanol (15 ml) dropwise, over 20 min. The reaction is monitored by TLC (20% EtOAc/Hexane)

during the addition, and cooled to room temperature as soon as all the starting material had been consumed. The reaction mixture is filtered through 'hyflo' and concentrated to dryness. The residue is purified by flash chromatography (4% MeOH/CH$_2$Cl$_2$ on silica gel) to give the title compound (0.47 g, 60%).

MS (EI+ion) m/z 275 M$^+$ $^1$H NMR (300M Hz, CDCl$_3$) δ 2.0 (m, 1H), 2.25–2.4 (m,3H), 2.6 (m, 1H), 3.2(1H), 5.75 (bs,2H), 7.1 (s,2H), 7.28 (m,3H), 7.38 (m,2H), 7.5 (m, 4H).

Preparation 7

3-Hydroxy-3-(4-naphth-2-yl-phenyl)piperidine 2-(4-Bromophenyl)naphthalene (9.29 g, 32.8 mmol) is placed in a round bottom flask under argon and dissolved in anhydrous THF (150 mL). The solution is cooled to −78° C. in a dry ice/acetone bath with stirring. A solution of n-butyl lithium (2.0M, 18.0 ml) is added dropwise and after fifteen minutes 1-benzyl-3-piperidone (8.14 g, 36.08 mmol) in 20 mL of THF is added dropwise with vigorous stirring. After 30 minutes the solution is allowed to warm to room temperature and quenched with saturated ammonium chloride (10 ml). The mixture is diluted with ethyl acetate (500 ml), washed with water and brine. The organic layer is dried over MgSO$_4$ and concentrated on a rotovap. The crude material is purified by silica gel flash column chromatography using 30% ethyl acetate in hexane as the eluant to yield 6.91 g (48%) of 1-benzyl-3-hydroxy-3 (4-naphth-2-yl-phenyl)piperidine as a white solid.

This intermediate (393 mg, 1.0 mmol) is dissolved in ethanol (50 mL) and water (20 mL) and 50 mg of Degussa type palladium on carbon (10%) added. The material is placed on a Parr hydrogenator overnight at 55 psi hydrogen. The resulting suspension is filtered through Celite and concentrated by rotovap. The material is purified by flash column chromatography using 10% methanol in methylene chloride with 1% triethylamine as the eluant to yield 0.118 g (39%) of 3-hydroxy-3-(4-naphth-2-ylphenyl)piperidine as a light yellow solid.

MS (EI+ion) m/z 303 M$^+$.

$^1$H NMR 300 MHz (CD$_3$OD)δ 1.67 (m, 1H), 1.89 (m, 1H), 2.10 (m, 1H), 2.79 (m, 2H), 2.94 (m, 1H), 3.06 (m, 1H), 3.18 (m, 1H), 7.08 (m, 2H), 7.38 (m, 2H) 7.65–7.42 (m, 2H), 7.76 (d, J=12 Hz, 2H), 7.89 (m, 2H), 8.08 (s, 1H).

In a like manner by the methods described in Preparation 7 the following compounds are prepared:

Preparation 8

3-Hydroxy-3-[(4-benzoxazo-2-yl)phenyl]piperidine
MS (FAB) m/z 295 (M+H)$^+$.

Anal. Calc. for C$_{18}$H$_{18}$N$_2$O$_2$.0.275 H$_2$O: C 72.24, H 6.25, N 9.36. Found: C 72.29, H 6.22, N 9.34.

Preparation 9

3-Hydroxy-3-[4-(2,3-dihydrobenzo[1.4]dioxin-6-yl) phenyl]piperidine
MS (EI+ion) m/z 311 M$^+$.

Preparation 10

3-Hydroxy-3-[4-(2-methoxyquinolin-6-yl)phenyl)] piperidine

MS (EI+ion) m/z 334 M$^+$.

Anal calc. for C$_{21}$H$_{22}$N$_2$O$_2$.H$_2$O: C 72.68, H 6.80, N 8.07 Found: C 72.65, H 6.77, N 8.19.

Preparation 11

3-Hydroxy-3-[4-(3-methoxyphenyl)phenyl]piperidine

MS (EI+ion): m/z 283 M$^+$ $^1$H NMR (300 MHz, CDCl$_3$)δ 1.65 (m, 1H), 1.85 (m, 3H), 2.6 (m, 1H), 2.9 (bs, 2H), 3.05 (m, 1H), 3.85 (s, 3H), 4.76 (bs, 1H), 6.88 (m, 1H), 7.25 (m, 3H), 7.35 (m. 1H), 7.55 (bs, 4H).

Preparation 12

3-Hydroxy-3-(biphen-4-yl)piperidine

MS (EI+ion) m/z 253 M$^+$

Anal calc. for C$_{17}$H$_{19}$NO.HCl.0.2H$_2$O: C 69.59, H 7.01, N 4.77 Found: C 69.60, H 6.88, N 4.76.

Preparation 13

3-hydroxy-3-[4-(2-bydroxynaphth-6-yl)phenyl] piperidine

By the method described in Preparation 7, 3-hydroxy-3-[4-(2-tert-butyltrimethylsilyloxynaphthalen-6-yl)phenyl]piperidine is prepared from 4-(2-tert-butyltrimethylsilyloxynaphthalen-6-yl)phenylbromide. This material (0.98 g, 2.4 mmol) is suspended in anhydrous tetrahydrofuran (40 ml) and treated with a solution of tetrabutylammonium fluoride (2.2 ml, 1M) dropwise. The reaction mixture is stirred 48 hrs at room temperature, diluted with methylene chloride (250 ml) and washed with saturated sodium chloride solution containing about 5 potassium carbonate. The resultant precipitated solid is collected, washed successively with ethyl acetate, a small amount of acetone and diethyl ether to give the title product (0.6 g, 95%).

MS (EI+ion) m/z 320 (M+H)$^+$.

Preparation 14

3-Hydroxy-3-(4-(2-hydroxyauinolin-6-yl)phenyl) piperidine

By the method described in Preparation 7, 1-benzyl-3-hydroxy-3-(4-(2-methoxyquinolin-6-yl)phenyl)piperidine is prepared from 6-(4-bromophenyl)-2-methoxyquinoline. This material (0.20 g, 0.471 mmol) is placed in a sealed tube under nitrogen with chloroform (5 mL), pyridine (0.02 ml, 0.075 mmol). and trimethylsilyliodide (0.107 ml, 0.754 mmol). The mixture is heated slowly to 55° C. in an oil bath for fifteen hours with stirring. The sealed tube is cooled to 0° C., opened and the contents diluted with methanol (50 ml). The solution is concentrated to dryness and the crude residue is purified by flash column chromatography using 10% methanol in methylene chloride to yield of 1-benzyl-3-hydroxy-3-(4-(2-hydroxyquinolin-6-yl)phenyl)piperidine as a yellow solid (0.1 g, 51%). The debenzylation is carried out as in preparation 1 to yield 3-hydroxy-3 -(4-(2-hydroxyquinolin-6-yl)-phenyl)-piperidine.

MS (FAB+ion) m/z 321 (M+H)+.

¹H NMR (300 MHz, DMSO-d₆) δ 1.24 (m, 1H), 1.58 (m, 1H), 1.73 (m, 1H), 1.97 (m, 1H), 2.78 (m, 4H), 3.35 (d, 2H, J=15 Hz), 5.38 (m, 1H), 6.52 (d, 1H, J=9 Hz), 7.36 (d, 1H, J=9 Hz), 7.65 (m, 4H), 7.83 (d, 1H, J=9 Hz), 7.95 (d, 2H, J=15 Hz).

Preparation 15

2-Methyl-2-(4-naphth-2-yl-phenyl)morpholine

4-Bromoacetophenone (20.0 g, 100 mmol) is placed in a flask under argon along with zinc iodide (1.6 g, 5 mmol) and trimethylsilyl cyanide (20 ml, 150 mmol). The mixture is stirred for 48 hours and then concentrated to dryness. The material is then treated by the procedures of Clark *J. Hetero. Chem.* 20, 1393 (1983), to give 2-(4-bromophenyl)-2-methylmorpholine. This material (2.17 g, 8.51 mmol) is dissolved in methylene chloride (25 ml) and treated with triethylamine (2.37 ml, 17 mmol) and Boc-anhydride (1.95 g, 8.93 mmol). The solution is stirred at 25° C. for three hours and then concentrated to dryness. Flash silica chromatography using 10% ethyl acetate in hexane as eluant yielded 2.4 g of the N-tert-butoxycarbonyl-2-(4-bromo phenyl)-2-methylmorpholine.

Naphth-2-yltrimethylstannane (0.617 g, 1.8 mmol, preparation 20) is dissolved in DMF (6 ml) and the above aryl bromide (0.630 g, 1.8 mmol) and tetrakistriphenylphosphine Pd(0) (0.102 g, 0.09 mmol) are added. The mixture is heated to 90° C. and stirred under argon for 4 hours. After cooling to room temperature the solution is stirred an additional 24 hours then poured into 10% ammonium hydroxide (30 ml) and methylene chloride (50 ml). The organic layer is separated and washed with water three times, then brine, and dried (MgSO₄). After concentration the material is purified by flash column chromatography using 10% ethyl acetate in hexane as eluant to yield 0.224 g of an orange oil. The oil is dissolved in methylene chloride (5 ml) and trifluoroacetic acid (2 ml) is added in portions. The solution is stirred for a total of 48 hours diluted with methylene chloride (50 ml) and saturated sodium bicarbonate (10 ml). The organic layer is washed with water and brine, dried (MgSO₄), and concentrated. Purification by flash column chromatography using 3% methanol in methylene chloride gave 0.098 g of 2-Methyl-2-(4-naphth-2-ylphenyl)morpholine (18%). ¹H NMR (300 MHz, CDCl₃) δ 1.43 (s, 3H), 2.77 (m, 1H), 3.02 (m, 2H), 3.57 (d, 1H, J=12 Hz), 3.70 (m, 2H), 7.49 (m, 1H), 7.55 (d, 3H, J=8.5 Hz), 7.76 (d,3H), 7.91 (m, 3H), 8.05 (s, 1H).

Preparation 16

4-[3-(4-Naphth-2-ylphenyl)]-1,2,5,6-tetrahydropyridine

3-Hydroxy-3-(4-naphth-2-yl-phenyl)piperidine (0.10 g, 0.33 mmol) is placed in a flask under argon. Concentrated HBr (5 ml) is added and a water cooled reflux condenser is attached. The solution is heated to reflux with stirring for 15 hours. After cooling to room temperature the mixture is diluted with water and the pH adjusted to 8 with saturated NaHCO₃ solution. The solution is extracted with ethyl acetate (200 ml) and methylene chloride (200 ml). The organic layers are combined, dried (MgSO₄), and concentrated. The material is purified by flash chromatography using 10% methanol in methylene chloride with 1% triethylamine to yield 0.046 g (49%) of 4-[3-(4-naphthalen-2-ylphenyl)]-1,2,5,6-tetrahydropyridine as a white solid.

MS (El+ion) m/z 285 M+

¹H NMR (300 MHz, CD₃OD) δ 2.37 (m, 2H), 3.04 (m, 2H), 3.76 (m, 2H), 6.43 (m, 1H), 7.49 (m, 4H), 7.76 (m, 3H), 7.91 (m, 3H), 8.10 (s, 1H).

In a like manner by the method described in Preparation 16, the following compound is prepared:

Preparation 17

3-[4-(2-Methoxyquinolin-6-yl)phenyl]-1,2,5,6-tetrahydropyridine

MS (El+ion) m/z 316 M+.

¹H NMR (300 MHz, CDCl₃) δ 2.33 (s, 2H), 2.56 (m, 2H), 3.30 (m, 2H), 4.01 (br s, 1H), 4.09 (s, 3H), 6.31 (m, 1H), 6.92 (d, 1H), 7.16 (d, 1H, J=6 Hz), 7.40 (d, 1H), 7.65 (d, 1H, J=8.2 Hz), 7.76 (d, 1H, J=7.8 Hz), 7.88 (m,1H), 8.00 (d,1H, J=8.8 Hz).

Preparation 18

2-[4-(1,2,5,6-Tetrahydropyridin-3-yl)phenyl]benzoxazole

A solution of 3-hydroxy-3-(4-benzoxazo-2-ylphenyl)piperidine (0.50 g, 1.7 mmol) and p-toluene sulfonic acid in 15 mL of anhydrous toluene is heated to remove toluene. The resulting residue is heated to 160° C. for 0.5 hours. The reaction mixture is cooled to room temperature and dissolved in methylene chloride and washed with 1N NaOH solution. The organic layer is dried over Na₂SO₄, filtered, concentrated and chromatographed with 5% to 10% gradient CH₃OH/CH₂Cl₂ to yield 2-[4-(1,2,5,6-tetrahydropyridin-3-yl)phenyl]benzoxazole (0.376 g, 80%) as a yellow solid.

MS (El+ion) m/z 276 M+

Anal calc. for C₁₈H₁₆N₂O.HCl. 0.125 H₂O: C 68.62, H 5.52, N 8.89 Found: C 68.39, H 5.42, N 8.76.

Preparation 19

1-Amino-2-(4-bromophenyl)propan-2-ol

Acetophenone (20.0 g, 0.1 mmol), trimethylsilyl cyanide (20 ml, 0.151 mmol) and zinc iodide (1.6 g, 5 mmol) are combined and stirred under argon for 48 hrs. The reaction is concentrated to a residue which is used without any further purification.

Crude 2-(4-bromophenyl)-2-trimethylsilyloxypropanionitrile from above is added to a 1.0M solution of lithium aluminum anhydride in THF (0.176 mol) under argon at room temperature. The reaction is stirred for 1 h then cooled to 0° C., quenched by the slow dropwise addition of water followed by 10% NaOH solution. The mixture is diluted with CH₂Cl₂ and the organic phase separated. The aqueous phase is extracted three times with CH₂Cl₂ and the combined organic phases are washed with saturated NaCl solution, dried and concentrated to dryness. The product is recrystallized from EtOAc/Hexane to give 13.8 g of 1-amino-2-(4-bromophenyl)propan-2-ol (60%).

Preparation 20

Naphth-2-yltrimethyl stannane tert-Butyllithium (12.5 ml, 21.25 mmol, 1.7M in pentane) is added dropwise to a stirred solution of 2-bromonaphthalene (2 g, 9.66 mmol) in anhydrous diethyl ether (40 ml) under argon at −78° C. The solution is stirred for 15 min and then treated with a 2.71M solution of trimethyltin chloride in dioxane (4.63 ml, 12.55 mmol). The heterogeneous mixture is warmed to room temperature, diluted with diethyl ether (150 ml) and treated with 10% $NH_4OH$ solution (90 ml) for 5 minutes. The two phases are separated and the organic phase is washed with water followed by brine, dried over $MgSO_4$ and concentrated to dryness. The oil is purified by flash silica chromatography (hexane) to give napthyltrimethyl stannane (2.69 g, 95.6%).

$^1$H NMR (300 MHz, $CDCl_3$) δ 0.2 (s, 9H,), 6.78 (m, 3H), 6.89 (d, J=7.8 Hz, 1 H), 7.13 (m, 2H), 7.29 (s, 1H).

The compounds of the present invention may be prepared by the following representative examples:

EXAMPLE 1

4-[3-Hydroxy-3-(4-naphth2-ylphenyl)piperidin-1-ylcarbonyl]- 3-hydroxy-3-carboxybutanoic acid 3-Hydroxy-3-(4-naphth-2-ylphenyl)piperidine (Preparation 7, 1.24 g, 4.09 mmol), 3-hydroxy-3, 4-bis(ethoxycarbonyl)butanoic acid (Preparation 1, 1.01 g, 4.09 mmol), EDC, (0.785 g, 4.09 mmol), 1-hydroxybenzotriazole (HOBT, 0.055 g, 2.05 mmol) and triethylamine (570 μL, 8.18 mmol) in THF or methylene chloride (150 mL) is stirred under argon overnight. The reaction mixture is diluted with $CH_2Cl_2$ or ethyl acetate and washed with water or 5% aqueous hydrochloric acid, saturated aqueous sodium bicarbonate, and brine. The organic layer is then dried over $MgSO_4$ or $Na_2SO_4$, filtered and concentrated. The crude product is purified by flash chromatography (using 60% ethyl acetate in hexane in this instance) to yield the diester intermediate, ethyl 4-[3-hydroxy-3 -(4-naphth-2-yl-phenyl)piperidin-1-ylcarbonyl]-3-hydroxy-3-ethoxycarbonylbutanoate (1.63 g, 75%) as a foam solid.

Anal. Calc. for $C_{31}H_{35}NO_7.0.425 H_2O$: C 68.79, H 6.68, N 2.59 Found: C 68.82, H 6.75, N 2.49.

The diester intermediate (1.63 g, 3.05 mmol) is dissolved in ethanol (50 mL) and treated with 10N NaOH (641 μL, 6.41 mmol). The reaction mixture is stirred at room temperature for 48 hours then optionally heated to 50° C. for 1 hour. The precipitate which is formed during the reaction is collected, dissolved in water and then filtered. 2N HCl is added to the aqueous solution until pH=3. A precipitate forms and the crude product is filtered and washed several times with water. The title compound (0.620 g, 43%) is purified by HPLC (10mm×25 cm Dynamax-60A 8 μM C-18 column) ramping from 0–100% acetonitrile in water over 50 min. with a flow rate of 10 ml/min.

MS (FAB+ion) m/z 478 $(M+H)^+$.

In a like manner by the methods described in Example 1 the following compounds are prepared:

EXAMPLE 2

4-(N-{2-[4-(Benzoxazol-2-yl)benzylexy]ethyl}-N-{2 -(3-phenylpropoxy) ethyl}carbamoyl)-3-hydroxy-3-carboxybutyric acid Anal. Calc. for $C_{33}H_{36}N_2O_9.0.25$ TFA: C 63.55, H 5.77, N 4.42 Found: C 63.44 H 5.88, N 4.52.

MS (FAB+ion) m/z 605 $(M+H)^+$

EXAMPLE 3

4-[2-Methyl-2-(4-naphthalen-2-yl-phenyl)morpholin-4 -ylcarbonyl]3-hydroxy-3-carboxybutanoic acid From the product of Preparation 15

Anal. Calc. for $C_{27}H_{27}NO_7.1.325 H_2O$: C 64.68, H 5.96, N 2.79 Found: C 64.66, H 5.63, N 2.82.

MS (FAB+ion) m/z 478 $(M+H)^+$.

EXAMPLE 4

4-[N-(2-α-Hydroxy-3-α-benzyloxycyclohexyl)-β-carbamoyl]-3-hydroxy-3-carboxybutanoc acid Anal. Calc. for $C_{19}H_{25}NO_8.1.225 H_2O$: C 54.66, H 6.63, N 3.36 Found: C 54.69, H 6.50, N 3.35.

MS (FAB+ion) m/z 396 $(M+H)^+$.

EXAMPLE 5

4-[2-α-(4-Benzoxazol-2-ylbenzyloxy)cyclohexyl-β-carbamoyl]-3 -hydroxy-3-carboxybutyric acid The title compound is prepared as described in example 1 except that solid NaOH (large excess) in ethanol/water (3:1) is used to hydrolyze the ester at room temperature. The title compound is purified by HPLC as described.

Anal. Calc. for $C_{26}H_{28}N_2O_8.0.45H_2O$: C 61.89, H 5.77, N, 5:55 Found: C 61.91, H 5.75, N, 5.44.

MS (FAB+ion) m/z 497 $(M+H)^+$

EXAMPLE 6

4-{N-[2-α-Hydroxy-3-α-(4-benzoxazol-2-ylbenzyloxy)cyclohex-1-yl]-β-carbamoyl}-3-hydroxy-3 -carboxybutyric acid The title compound is prepared as described in example 1 except that 1N NaOH is used to hydrolyze the ester at room temperature. Upon completion (TLC analysis) the solution is acidified and the resultant precipitate is collected (filtration or centrifugation) and purified by washing with copious amounts of water.

Anal. Calc. for $C_{26}H_{28}N_2O_9.0.72 H_2O$: C 59.43, H 5.65, N 5.33 Found: C 59.43, H 5.66, N 5.25.

EXAMPLE 7

(±)-4-[-trans,trans-N-(3, 7, 11-trimethyl-2, 6, 10-dodecatrien-1-yl)carbamoyl]-3-hydroxy-3-carboxybutyric acid The title compound is prepared as described in example 1 except that LiOH (10 equiv.) is used to hydrolyze the ester. Upon completion (TLC analysis) the solution is acidified and extracted into ethyl acetate. The product is obtained upon crystallization with hexane.

Anal. Calc. for $C_{21}H_{33}NO_6$: C 63.78, H 8.41, N 3.54 Found: C 63.64, H 8.30, N 3.63.

EXAMPLE 8

4-[3-Hydroxy-3-(4-(2-hydroxyquinolin-6-yl)phenyl) piperidin-1
-ylcarbonyl]-3-hydroxy-3-carboxybutanoic acid, disodium salt 4-[3-Hydroxy-3-(4-(2-hydroxyquinolin-6-yl)phenyl)piperidin-1-ylcarbonyl]- 3-hydroxy-3-carboxybutanoic acid diethyl ester (75 mg, 0.14 mmol) is prepared in the manner described above from the product of Preparation 14 and treated with 10N NaOH (55 μL, 0.55 mmol). After stirring overnight at room temperature, water is added to dissolve the precipitate. The resulting solution is stirred for an additional 24 hours then concentrated. The solid is collected, washed repeatedly with hot ethanol then dissolved in water and filtered to remove any remaining insoluble particles. The aqueous solution is lyophilized and the product (40 mg, 43%) obtained as the sodium salt.

Anal. Calc. for $C_{26}H_{24}N_2O_8$ $Na_2.H_2O.3NaOH$: C 46.16, H 4.32, N 4.14 Found: C 46.06, H 4.20, N 3.88.

MS (FAB+ion) m/z 539 (M+H)

In a like manner by the methods described in Example 8 the following compounds are prepared:

EXAMPLE 9

4-{2-[4-(Benzoxazol-2-yl)benzyloxymethyl] pyrrolidin-1-ylcarbonyl}-3-hydroxy-3-
carboxybutanoic acid, disodium salt From the product of Preparation 5.

Anal. Calc. for $C_{25}H_{24}N_2.0.75$ $H_2O$: C 55.61, H 4.26, N 5.19 Found: C 55.60, H 4.68, N 5.04.

EXAMPLE 10

4-[3-Hydroxy-3[4-(2,3-dihydrobenzo[1.4] dioxin-6-yl)phenyl]piperidin-1-ylcarbonyl}-
3-hydroxy-3-carboxybutanoic acid, disodium salt From the product of Preparation 9.

Anal. Calc. for $C_{25}H_{25}NO_9Na_2.1$ $NaOH1$ $H_2O$: C 51.11, H 4.80, N 2.38 Found: C 51.06, H 4.80, N 2.54.

MS (FAB+ion) m/z 530 (M+H)$^+$

EXAMPLE 11

4-{3-Hydroxy-3-[4
-(2-methoxyquinolin-6-yl)phenyl]piperidin-1
-ylcarbonyl}-3-hydroxy-3-carboxybutanoic acid, disodium salt From the product of Preparation 10.

Anal. Calc. for $C_{27}H_{26}$ $N_2O_8$ $Na_2.2.425$ $H_2O$: C 54.40, H 5.22, N 4.70 Found: C 54.39, H 5.01, N 4.40.

MS (FAB+ion) m/z 509 (M+H)$^+$.

EXAMPLE 12

4-{3-[4-(2-methoxyquinolin-6
-yl)phenyl]-1,2,5,6-tetrahydro-pyridylcarbonyl}-3
-hydroxy-3-carboxybutanoic acid, disodium salt From the product of Preparation 17.

MS (FAB+ion) m/z 535 (M+H)$^+$.

EXAMPLE 13

4-[3-(4-naphthalen-2-yl-phenyl)-1,2,5,6
-tetrahydropyridyl-carbonyl]-3-hydroxy3-
carboxybutanoic acid, disodium salt From the product of Preparation 16.

MS (FAB+ion) m/z 504 (M+H)$^+$.

EXAMPLE 14

4-{3-(4-(6-Hydroxynaphth-2-yl)phenyl)-
3-hydroxypiperidin-1-ylcarbonyl]-3-hydroxy-3-
carboxylbutanoic acid, trisodium salt The title compound is prepared as described in Example 1 from the products of Preparation 13, except that 1N NaOH is used to hydrolyze the intermediate diester. Upon concentration, the precipitate is collected (filtration or centrifugation) and purified by repeatedly washing with ethanol (hot if necessary) followed by ether. The product is dried under high vacuum.

Anal. Calc. for $C_{27}H_{24}NO_8Na_3.2.0H_2O$: C 54.46, H 4.74, N 2.35 Found: C 54.56, H 4.81, N 2.26.

MS (FAB+ion) m/z 560 (M+H)$^+$

In a like manner, by the methods described in example 14, the following compounds are prepared:

EXAMPLE 15

4-[3-(4-(Benzoxazol-2-yl)phenyl)-1, 2, 5,
6-tetrahydropyridylcarbonyl]-3-hydroxy-3-
carboxybutanoic acid, disodium salt From the product of Preparation 18.

Anal. Calc. for $C_{24}H_{20}N_2O_7Na_2.0.9H_2O$: C 56.45, H 4.30, N, 5.49 Found: C 56.46, H 4.11, N, 5.33.

MS (FAB+ion) m/z 495 (M+H)$^+$.

EXAMPLE 16

4-{N-[2-α-Hydroxy-3-α-(4-benzoxathiazol-2
-ylbenzyloxy)cyclohex-1-yl]-β-carbamoyl}-3-
hydroxy-3 -carboxybutanoic acid, disodium salt Anal. Calc. for $C_{26}H_{26}N_2O_8SNa_2.2.15H_2O$: C 51.09, H 5.00, N ,4.58 Found: C 51.08, H 4.90, N, 4.51

MS (FAB+ion) m/z 573 (M+H)$^+$.

EXAMPLE 17

4-[3-(4-Benzoxazol-2-ylbenzyloxy)piperidin-1-
ylcarbonyl]-3 -hydroxy-3-carboxypentanoic acid,
disodium salt From the product of Preparation 2.

Anal. Calc. for $C_{25}H_{24}N_2O_8Na_2.1.5$ $H_2O$: C 54.25, H 4.92, N 5.06 Found: C 54.00, H 4.64, N 4.94.

EXAMPLE 18

4-(N-Biphen-4-ylcarbamoyl)-3-hydroxy-3
-carboxybutanoic acid, disodium salt

Anal. Calc. for $C_{18}H_{15}NO_6Na_2.1.775$ $H_2O$: C 51.56, H 4.46, N 3.34 Found: C 51.55, H 3.98, N 3.36.

MS (FAB+ion) m/z 388 (M+H)$^+$.

EXAMPLE 19

4-[3-(4-(Benzoxazol-2-yl)benzyloxymethyl)piperidin-1-ylcarbonyl]-3-hydroxy-3-carboxybutanoic acid, disodium salt From the product of Preparation 3.

Anal. Calc. for $C_{26}H_{26}N_2O_8Na_2.1.425\ H_2O$: C 55.16, H 5.14, N 4.95 Found: C 55.14, H 5.06, N 4.77

EXAMPLE 20

4-[3-(4-(Benzoxazol-2-yl)benzyloxy)pyrrolidin-1-ylcarbonyl]-3-hydroxy-3-carboxybutanoic acid, disodium salt From the product of Preparation 4.

Anal. Calc. for $C_{24}H_{22}N_2O_8Na_2.1.525\ H_2O$: C 53.39, H 4.68, N 45.19 Found: C 53.38, H 4.61, N 5.32

EXAMPLE 21

4-[3-Hydroxy-3-(4-benzoxazol-2-ylphenyl)piperidin-1-ylcarbonyl]-3-hydroxy-3-carboxybutanoic acid, disodium salt From the product of Preparation 8.

Anal. Calc. for $C_{24}H_{22}N_2O_8Na_2.1.925\ H_2O$: C 52.69, H 4.76, N 5.12 Found: C 52.68, H 4.36, N 4.87.

MS (FAB+ion) m/z 579 (M+H)$^+$.

EXAMPLE 22

3-{N-[1-(4-Benzoxazol-2-ylbenzyloxy)but-2-yl]carbamoyl}-3-hydroxy-3-carboxybutanoic acid, disodium salt Anal. Calc. for $C_{24}H_{24}N_2O_8Na_2.3.0H_2O$: C 50.71, H 5.32, N 4.93 Found: C 50.51, H 5.18, N 4.86.

MS (FAB+ion) m/z 515 (M+H)$^+$.

EXAMPLE 23

3-{N-[4-(Benzoxazol-2-yl)benzyl]carbamoyl}-3-hydroxy-3-carboxybutanoic acid, disodium salt Anal. Calc. for $C_{20}H_{16}N_2O_7Na_2.1.35H_2O$: C 51.48, H 4.04, N 6.00 Found: C 51.48, H 3.99, N 5.93.

MS (FAB+ion) m/z 443 (M+H)$^+$.

EXAMPLE 24

4-[3-Hydroxy-2-(3'-methoxybiphenyl-4-yl)piperidin-1-ylcarbonyl]-3-hydroxy-3-carboxybutanoic acid, disodium salt From the product of Preparation 11.

Anal. Calc. for $C_{24}H_{25}NO_8Na_2.1H_2O$: C 55.49, H 5.24, N 2.70 Found: C 55.42, H 4.95, N 2.55.

MS (FAB+ion) m/z 502 (M+H)$^+$.

EXAMPLE 25

4-[3-(Biphenyl-4-yl)-3-hydroxypiperidine-1-ylcarbonyl]-3-hydroxy-3-carboxybutanoic acid, disodium salt From the product of Preparation 12.

Anal. Calc. for $C_{23}H_{23}NO_7Na_2.1.3H_2O$: C 55.88, H 5.21, N 2.83 Found: C 55.86, H 5.13, N 2.85.

MS (FAB+ion) m/z 472 (M+H)$^+$.

EXAMPLES 26A AND B

4-[2-α-(4-Styrylphenyl)cyclohex-4-enyl-β-carbamoyl]-3-hydroxy-3-carboxybutyric acid, diastereomers A and B 6-α-(4-Styrylphenyl)cyclohexyl-4-enyl-β-amine (Preparation 6) is coupled to diethycitrate as described in example 1. The resultant diesters are recrystallized from EtOAc/Hexane to give one diasteriomeric pair of enantiomers in a greater than 90% purity, characterized as the long retention time diastereomer (HPLC). The mother liquors are concentrated and purified by HPLC to isolate the second diastereomeric pair of enantiomers having a shorter retention time than the crystallized material.

The diastereomer with longer HPLC retention time is hydrolyzed with 1N NaOH in ethanol/water (3:1 ). Upon completion (TLC analysis) the solution is acidified and the mixture saturated with NaCl then extracted with $CH_2Cl_2$. The organic extracts are concentrated to give an oily solid which is triturated with $Et_2O$. The supernatent liquid is concentrated to give 4-[2-trans-(p-β-styrylphenyl) cyclohexyl-4-enylcarbamoyl]-3-hydroxy-3-carboxybutyric acid, diastereomer 26A.

Anal. Calc. for $C_{26}H_{27}NO_6.1.4\ H_2O$: C 65.78, H 6.33, N 2.94 Found: C 66.16, H 6.80, N 2.94

MS (FAB+ion) m/z 450 (M+H)$^+$.

The diastereomer with shorter HPLC retention time is hydrolyzed as above and the di sodium salt of the acid is isolated by decantation of the supernatent liquid. Trituration with a mixture of diisopropyl ether and ethanol affords 4-[2-trans-(p-β-styrylphenyl)cyclohexyl-4-enylcarbamoyl]-3-hydroxy-3 -carboxybutyric acid as the disodium salt, diastereomer 26B.

Anal. Calc. for $C_{26}H_{25}NO_6Na_2.2.3H_2O$: C 58.38, H 5.58, N 2.62 Found: C 57.77, H 5.06, N 2.54.

MS (FAB+ion) m/z 494 (M+H)$^+$.

EXAMPLE 27

3-(N-{2-α-[4-(Benzoxazol-yl)benzyloxy]cyclohexyl}-β-carbamoyl)-3 -carboxybutanoic acid A solution of 2-α-[4-(benzoxazol-2-yl)benzyloxy]-cyclohexyl-β-amine (220 mg, 0.68 mmol) in anhydrous $CH_2Cl_2$ (10 mL) is treated with tricarballylic acid (0.131 g, 0.74 mmol), EDC (0.207 g, 1.08 mmol), HOBT (0.155 g, 1.15 mmol) and triethylamine (0.3 ml, 2.15 mmol) under argon. The resulting mixture is stirred overnight at room temperature then diluted with 100 ml $CH_2Cl_2$ and extracted with 1N HCl solution. The organic layer is separated, dried over $MgSO_4$, filtered, concentrated and purified by HPLC (10mm×25 cm Dynamax-60A 8 μM C-18 column) ramping from 0–100% acetonitrile in water over 50 min. with a flow rate of 10 ml/min. After lyophilization, the title product (36 mg, 10%) is obtained.

Anal. Calc. for $C_{25}H_{23}N1O_7Na_2.0.5H_2O$: C 63.79, H 5.97, N 5.72 Found: C 63.78, H 6.02, N 6.05.

MS (FAB+ion) m/z 481 (M+H).

EXAMPLE 28

3-Hydroxy-3-{-N-[2-hydroxy-2-(4-naphthalen-2-yl-phenyl)prop-2-yl]carbamoyl} pentandioic acid, disodium salt 1-(3-Dimethylaminopropyl)-3-ethyl carbodiimide hydrochloride (0.833 g, 4.34 mmol) followed by 1-hydroxybenzotriazole hydrate (0.66 g, 4.35 mmol), 3 -hydroxy-3,4-bis (ethoxycarbonyl)butanoic acid (1.08 g, 4.35 mmol) in THF (50 ml) and triethylamine is added to a stirred solution of 1-amino-2-(4-bromophenyl) propan-2-ol (Preparation 19, 1 g, 4.35 mmol) in THF (45 ml). The reaction mixture is stirred at ambient temperature for 18 hrs, diluted with $CH_2Cl_2$ and washed with saturated $NaHCO_3$ solution followed by saturated NaCl solution. The organic layer is dried over $MgSO_4$, concentrated and purified by flash chromatography (2% MeOH/$CH_2Cl_2$) to give 1-[2-(4 -bromophenyl)-2-hydroxy-propyl]-3-hydroxy-2,5-dioxopyrrolidin-3-ylacetic acid, ethyl ester (0.5 g, 28% yield); MS (FAB+ion) m/z 414/416 $(M+H)^+$ and 4-[2-(4 -bromophenyl)-2-hydroxypropylcarbamoyl]-3-hydroxy-3-methyl butyric acid ethyl ester (0.94 g, 50% yield); MS (FAB+ion) m/z 460/462 $(M+H)^+$.

Naphthyltrimethyl stannane (Preparation 20, 0.31 mmol, 0.091 g), tetrakis(triphenyl phosphine)Palladium(O) (15 mg, 13 mmol), and ethyl 1-[2-(4-bromophenyl)-2-hydroxypropyl]-3-hydroxy-2,5 -dioxopyrrolidin-3-ylacetate (0.12 g, 0.26 mmol) in anhydrous DMF are heated at 95° C. under an inert atmosphere for 3.5 hr. The reaction mixture is partitioned between EtOAc and saturated NaCl solution. The organic phase is washed several times with further quantities of saturated NaCl solution, dried ($Na_2SO_4$) and concentrated. The residue is purified by flash chromatography (EtOAc/Hexane, 35 to 50%), to yield ethyl 1 -[2 -(4- naphthalen-2-yl-phenyl-2-hydroxypropyl]-3-hydroxy-2,5-dioxopyrrolidin-3 -ylacetate (66 mg, 55%).

The ester is hydrolyzed as described in example 14 to give of the title compound (65 mg, 51%).

Anal. Calc. for $C_{25}H_{23}NlO_7Na_2 \cdot 1.5H_2O$: C 57.47, H 5.02, N 2.68 Found: C 57.36, H 5.21, N 2.68.

MS (FAB+ion) m/z 496 $(M+H)^+$.

EXAMPLE 29

5-{2-α-[4-(Benzoxazol-2-yl)benzyloxy]cyclohex-1-yl-β-amino}-3-carboxypentanoic acid A solution of DMSO (0.25 mL, 3.5 mmol) in 15 mL of THF is cooled to −78° C. and treated with oxalyl chloride (0.27 mL, 3.1 mmol). After 10 minutes, a solution of 2, 2-diethoxy ethanol in THF is added. The reaction mixture is stirred for 15 minutes at −78° C. and treated with triethyl amine (1.88 mL, 13.5 mmol). The resulting solution is warmed to 0° C. In a separate flask, diethoxy (diethyl succinyl) phosphine oxide (1.3 g, 4.19 mmol) in THF is added to 0° C. suspension of 60% NaH (0.16 g, 4.05 mmol) in THF. After stirring for 1 hour at 0° C., the resulting solution is added to the preformed aldehyde solution via a cannula. The reaction mixture is stirred for 2 hours and then poured into ether/water mixture. Aqueous layer is separated and further extracted with ether. Organic layers are combined, dried over $MgSO_4$, and flash chromatographed on silica gel with 8:2 hexane/ethyl acetate to yield diethyl 2 -(2, 2-diethoxy ethenyl) succinate (0.6 g, 77%).

Diethyl 2-(2, 2-diethoxy ethenyl) succinate (0.6 g, 2.1 mmol) is hydrogenated under 45 psi of $H_2$ atmosphere for 1½ days in 50 mL of EtOAc over 10% Pd/C to yield diethyl 2-(2, 2-diethoxy ethyl) succinate (0.33 g, 55%).

Diethyl 2-(2, 2-diethoxy ethyl) succinate (0.33 g, 1.1 mmol) dissolved in 20 mL of THF is treated with 2 drops of concentrated HCl and stirred for 45 minutes at room temperature. The reaction mixture is diluted with 100 mL of ether, dried over $MgSO_4$, filtered, and concentrated to yield diethyl 2-(2-oxoethyl) succinate (0.23 g, 98%).

A solution of acetic acid salt of 2-α-[4-(benzoxazol-2-yl)benzyloxy]-cyclohexyl-β-amine (0.46 g, 1.11 mmol) and diethyl 2-(2-oxoethyl) succinate (0.24 g, 1.11 mmol) in methanol is treated with $NaBH_3CN$ (0.07 g, 1.11 mmol) at room temperature for 4 hours. Removal of solvent followed by silica gel flash chromatography with 10% MeOH in $CH_2Cl_2$ gives 140 mg (24%) of the diethyl ester.

The diester is hydrolyzed by the method described in example 2 except the reaction mixture is acidified to pH 2 with HCl/EtOH solution and concentrated in vacuo. The title compound (30 mg, 24%) is purified via HPLC (10 mm×25cm Dynamax-60A 8 μM C 18 column) ramping from 20 to 80% $CH_3CN$ in $H_2O$ over 50 min. with a flow rate of 10 mL/min.

Anal. Calc. for $C_{26}H_{30}N_2O_6 \cdot 1.3H_2O$: C 63.74, H 6.71 N, 5.72 Found: C 63.74, H 6.45, N, 5.91.

MS (FAB+ion) m/z 467 (M+H).

EXAMPLE 30

3-(R)-(N-{2-α-[4-(Benzoxazol-2-yl)benzyloxy]cyclohexyl}-β-carbamoylaza)-3-carboxypropanoic acid A solution of 2-α-[4-(Benzoxazol-2-yl)benzyloxy]-cyclohexyl-β-amine (400 mg, 1.24 mmol), triphosgene (123 mg, 0.41 mmol) and triethylamine (106 μL, 4.35 mmol)in 15 mL $CH_2Cl_2$ is stirred at room temperature for 5 hours. Triethylamine (173 μL, 1.24 mmol) and D-aspartic acid dimethyl ester hydrochloride (245 mg, 1.24 mmol) is added. The resulting mixture is heated to 4020 C. and stirred overnight. The reaction mixture is washed with saturated sodium bicarbonate solution and the organic layer is dried over $MgSO_4$, filtered and concentrated. The crude material is purified by flash chromatography (1% methanol/methylene chloride) to give the intermediate diester (490 mg, 77%) as a white solid.

Lithium hydroxide monohydrate (501 mg, 11.9 mmol) is added to a solution of the intermediate diester (490 mg, 0.96 mmol) in THF/methanol/water (9:3:3) and stirred overnight at room temperature. The reaction mixture is concentrated and the contents partially dissolved in hot water (30 mL). After cooling, the solution is extracted with diethyl ether. The aqueous layer is partially concentrated and conc. HCl is added dropwise until the pH approximates 2. The acidic solution is cooled (about 5° C.) for 30 minutes. The crystallized product (215 mg, 46%) is filtered, washed with water and dried on the vacuum pump overnight.

Anal. Calc. for $C_{25}H_{27}N_3O_7 \cdot 0.5 H_2O$: C 61.22, H 5.75, N 8.62 Found: C 61.27, H 5.71, N 8.62.

In a like manner by the method described in Example 30 the following compounds are prepared using the corresponding amine:

EXAMPLE 31

3-{N-[4-(Benzoxazol-2-yl)phenylmethyl]carbamoylaza}-3-carboxypropanoic acid

Anal. Calc. for $C_{19}H_{17}N_3O_6 \cdot 1.46H_2O$: C 55.71, H 4.90, N 10.26 Found: C 55.70, H 4.61, N 10.05.

EXAMPLE 32

3-(S)-(N-{2-α-[4-(Benzoxazol-2-yl)benzyloxy]cyclohexyl}-β-carbamoylaza)- 3-carboxypropanoic acid Anal. Calc. for $C_{25}H_{27}N_3O_7$: C 62.36, H 5.65, N 8.73 Found: C 62.08, H 5.71, N 8.74.

EXAMPLE 33

3-(S)-{3-[4-(benzoxazol-2-yl)phenyl]-1, 2, 5, 6-tetrahydropyrid-1-ylcarbonylaza}-3-carboxypropanoic acid From the product of Preparation 18.

Anal. Calc. for $C_{23}H_{21}N_3O_6 \cdot 0.5H_2O \cdot 0.4$ EtOH: C 61.70, H 5.27, N 9.07 Found: C 61.78, H 5.29, N 9.17.

EXAMPLE 34

3-(R)-{3-[4-(benzoxazol-2-yl)phenyl]-1, 2, 5, 6-tetrahydropyrid-1-ylcarbonylaza}-3-carboxypropanoic acid From the product of Preparation 18.

Anal. Calc. for $C_{23}H_{21}N_3O_6 \cdot 0.76$ EtOH: C 62.61, H 5.47, N 8.94 Found: C 62.35, H 5.51, N 8.93.

EXAMPLE 35

3-(S)-{N-[2-α-(4-Styrylphenyl)cyclohex-4-enyl]-β-carbamoylaza}-3-carboxy propanoic acid Anal. Calc. for $C_{25}H_{26}N_2O_5 \cdot 0.5\ C_6H_{14}O$: C 69.26, H 6.85, N 5.77 Found: C 69.34, H 6.93, N 5.56.

MS (EI+ion) m/z 435M$^+$.

Various tests have been carried out to show the ability of the compounds of the present invention to exhibit pharmacological responses that can be correlated with activity in humans. These tests involve such factors as the effect of the compounds of Formula I to inhibit the synthesis of squalene. It has been found that compounds within the scope of this invention when tested using the following procedures show a marked activity for the inhibition of squalene synthase and hence are believed to be useful in the treatment of cholesterol-related disorders.

Squalene Synthase Inhibition Assay

The squalene synthase assay used is described by Amin et al. in "Bisphosphonates Used for the Treatment of Bone Disorders Inhibit Squalene Synthase and Cholesterol Biosynthesis," Journal of Lipid Research, 33, 1657–1663 (1992).

I. Preparation of Assay Substances:

A) Test Solutions:

Test solutions are prepared fresh in 100% DMSO or dH$_2$O. Subsequent dilutions are made in the same solvent. Compounds are tested initially at 1 µM (final concentrations).

B) Assay Buffers:

Potassium Phosphate (50 mM,) pH 7.4, and HEPES (4-(2-hydroxyethyl)- 1-piperazineethanesulfonic acid, 50 mM) pH 7.4 stock buffers are prepared and stored at 4° C. until use.

C) Microsomal Enzyme Preparation:

Fresh livers from male Sprague-Dawley rats (Taconic Farms, Germantown, N.Y.) weighing 150–200 g are collected after exsanguination. All subsequent procedures are performed at 4° C. The liver is homogenized in the assay buffer (50 mM, pH 7.4). Cellular fractions are separated as described by Popjak, G. in "Enzymes of sterol biosynthesis in liver and intermediates of sterol biosynthesis," *Meth. Enzymol.* 15 393–454 (1969). Microsomes are prepared by centrifugation (100,000 g) and then resuspended in the assay buffer. Microsomes are rehomogenized with a motor-driven Teflon pestle to yield a uniform suspension (~30 mg protein/ ml), aliquoted, and stored at −80° C. until use.

II. Squalene Synthase Assay

The procedure is a modification of those described by Popjack (vida supra) and Poulter et al. in "Squalene synthase. Inhibition by ammonium analogues of carbocationic intermediates in the conversion of presqualene diphosphate to squalene" *J. Am. Chem. Soc.* 111, 3734–3739 (1989). The assay is performed in 1 ml of 50 mM assay buffer, pH 7.4, containing 10 mM MgCl$_2$, 0.5 mM NADPH, microsomes (30 µg protein), a test compound dissolved in distilled water or dimethylsulfoxide, and substrate [$^3$H]FPP (0.5 µM, 0.27 Ci/mmol) in a 16×125 mm glass screw-cap tube. All components except [3H]FPP are preincubated for 10 min. at 37° C. The reaction is initiated by the addition of [$^3$H]FPP. After 10 min at 37° C., the reaction is terminated by the addition of 1 ml 15% KOH in ethanol. The tubes are incubated at 65° C. for 30 min. to solubilize proteins. The mixture is extracted with 5 ml petroleum ether for 10 min. After freezing the lower aqueous phase, the organic phase is transferred to glass tubes containing 2 ml distilled water. After washing the lower aqueous phase is frozen and the petroleum ether phase is removed and counted with 10 ml Ready Safe liquid scintillation cocktail using a Beckman LS- 9000 scintillation counter. DPM values are adjusted against a blank (no enzyme).

The difference in radioactivity in the presence and absence of the test compound is used to determine the level of inhibition. The IC$_{50}$ values are calculated using a linear regression program of Tallarida and Murray (1987). Tallarida, R. J. and Murray, R. B. Manual of pharmacologic calculations with computer programs. Springer-Verlag, 1987.

The following table shows examples of representative compounds of this invention and their test results as determined in the squalene synthase inhibition assay.

TABLE

| | | HEPES buffer IC$_{50}$ |
|---|---|---|
| Example 5 | [structure: benzoxazole-phenyl-CH2-O-cyclohexyl-NH-C(O)-CH2-C(OH)(CO2H)-CH2-CO2H] | 0.19 µM |
| | [structure: benzoxazole-phenyl-CH2-O-cyclohexyl-NH-C(O)-CH2-C(OH)(CO2Et)-CH2-CO2Et] | 10 µM |
| Example 22 | [structure: benzoxazole-phenyl-CH2-O-CH2-CH(Et)-NH-C(O)-CH2-C(OH)(CO2Na)-CH2-CO2Na] | 77 nM |
| Example 19 | [structure: benzoxazole-phenyl-CH2-O-CH2-piperidinyl-N-C(O)-CH2-C(OH)(CO2Na)-CH2-CO2Na] | 51 nM |
| Example 12 | [structure: 2-methoxyquinoline-phenyl-C(OH)-piperidinyl-N-C(O)-CH2-C(OH)(CO2Na)-CH2-CO2Na] | 36 nM |
| Example 1 | [structure: naphthyl-phenyl-C(OH)-piperidinyl-N-C(O)-CH2-C(OH)(CO2H)-CH2-CO2H] | 27 nM |
| Example 24 | [structure: MeO-phenyl-phenyl-C(OH)-piperidinyl-N-C(O)-CH2-C(OH)(CO2Na)-CH2-CO2Na] | 0.1 µM |

TABLE-continued

| | HEPES buffer IC$_{50}$ |
|---|---|
| Example 30 [structure: benzoxazole-phenyl-CH$_2$-O-cyclohexyl-NH-C(O)-N(H)-CH(CO$_2$H)-CH$_2$-CO$_2$H] | 2.6 μM |
| Example 28 [structure: naphthyl-phenyl-C(OH)(CH$_3$)-CH$_2$-NH-C(O)-C(OH)(CH$_2$CO$_2$Na)-CH$_2$CO$_2$Na] | 0.1 μM |

Compounds within the scope of Formula I have been tested by the foregoing assay procedures and exhibit marked squalene synthase inhibition activity and are useful as hypocholesterolemic or hypolipidemic agents by virtue of their ability to inhibit the biosynthesis of cholesterol. Having such ability, the compounds are incorporated into pharmaceutically acceptable carriers and administered to a patient in need of such cholesterol biosynthesis inhibition. These pharmaceutical formulations contain at least one compound according to this invention.

Treatment with a combination of an HMG-CoA reductase inhibitor and a squalene synthase inhibitor would have a synergistic effect on inhibiting cholesterol biosynthesis. Inhibiting the squalene synthase enzyme and the HMG-CoA reductase enzyme at the same time would most closely resemble the physiological conditions of cholesterol homeostasis. A squalene synthase inhibitor could keep cellular concentrations of farnesyl diphosphate high enough for the synthesis of the small amounts of dolichol, ubiquinone, and the farnesylated proteins required by the cell. This would maintain some feedback regulation of the HMG-CoA reductase enzyme and allow smaller amounts of the HMG-CoA reductase inhibitor to be used.

Other combinations with a squalene synthase inhibitor which could have a synergistic effect for controlling undesirable cholesterol levels in the body include niacin, anti-hyperlipoproteinemic agents such as gemfibrozil, cholesterol absorption inhibitors, bile acid sequestrants, antioxidants and lipoxygenase inhibitors.

Compounds of the present invention which inhibit squalene synthase may also be of use in combating fungal infections in animals and humans. They may be useful in the treatment of variety of systemic infections and treating tropical infections. They may be also useful as prophylactic agents to prevent systemic and tropical fungal infections. Prevention of fungal overgrowth during antibiotic treatment may also be desirable in some disease syndromes.

Compounds may be tested under a spectrum of activity against a panel of representative yeasts, filamentous fungi and bacteria. The ability of compounds of the invention to inhibit the enzyme squalene synthase in fungi and bacteria may be demonstrated in vitro using ($^{14}$C)FPP as a substrate under assay conditions similar to those described by S. A. Biller et al. in *J. Medicinal Chemistry* 31, 1869–1871 (1988), or Amin et al. *Journal of Lipid Research*, 33, 1657–1663 (1992).

The in vitro evaluation of the anti-fungal activity of compounds of the invention can be performed by determining the minimum inhibitory concentration (MIC) which is the concentration of the test compound in a suitable medium at which growth of a particular microorganism fails to occur.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from about 0.1 to about 1000 mg/day, and preferably from about 10 mg to about 100 mg/day, or from about 0.1 mg to about 50 mg/kg of body weight per day and preferably from about 0.1 to about 20 mg/kg of body weight per day and may be administered in several different dosage units. Higher dosages, on the order of about 2× to about 4×, may be required for oral administration.

We claim:

1. A compound of the formula:

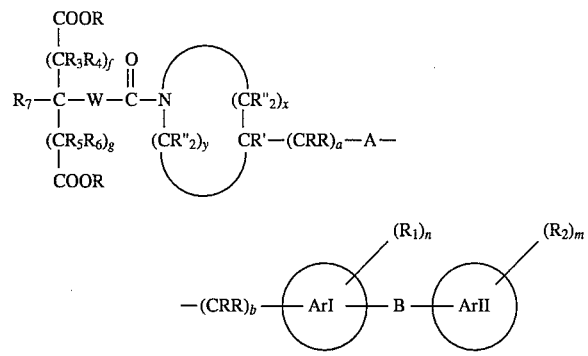

where:

A is O, S, NR, SO, $SO_2$ or a bond;

B is $(CRR)_{1-2}$, O, S, NR, SO, $SO_2$, RC=CR, C≡C, O=C or a bond;

W is a bond, $(CRR)_h$, or NR;

R is hydrogen or $C_{1-6}$ alkyl;

R' and R" are independently hydrogen, $C_{1-6}$ alkyl, $C_{1-6}$ alkoxy, hydroxy, halo, trifluoromethyl or phenyl;

R' and R" together may form a double bond;

$R_1$ and $R_2$ are independently hydrogen, $C_{1-6}$ alkyl, $C_{1-6}$ alkoxy, hydroxy, halo, trifluoromethyl or phenyl;

$R_3$, $R_4$, $R_5$ and $R_6$ are independently hydrogen or $C_{1-6}$alkyl;

$R_7$ is H, NRR or OH and when W is $(CRR)_h$ then $R_7$ is OH;

one of $R_3$, $R_4$, $R_5$, $R_6$ or $R_7$ is OH;

Ar I is phenylene;

Ar II is selected from phenyl, pyridyl, naphthyl, benzoxaxolyl, quinolinyl or benzothiazolyl;

a and b are independently 0–3;

a+b is 0–4;

f is 0–2;

g is 0–2;

h is 1–2;

m and n are independently 0–2;

x is 1–6;

y is 0–2;

x+y is 3–6; and its stereoisomers, enantiomers, diastereoisomers and racemic mixtures; or a pharmaceutically acceptable salt thereof.

2. A compound according to claim 1 of the formula:

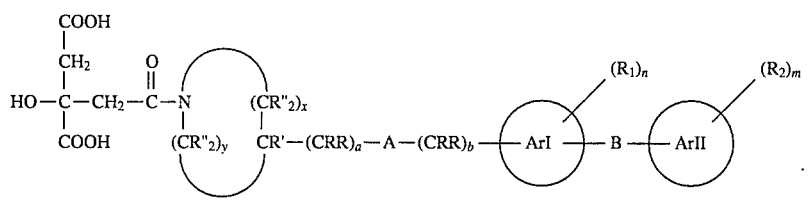
3. A compound according to claim 1 of the formula:
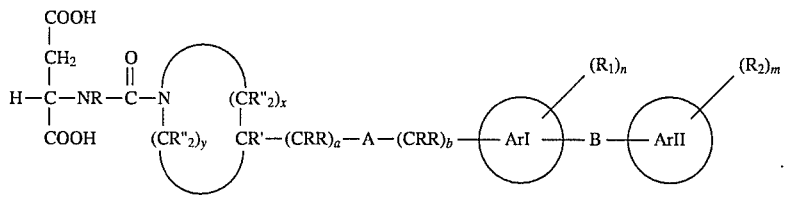
4. A compound according to claim 2 of the formula:
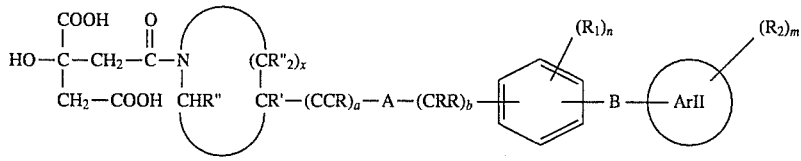
ArII is selected from phenyl, pyridyl, naphthyl, benzoxaxolyl, quinolinyl or benzothiazolyl.
5. A compound according to claim 4 of the formula:
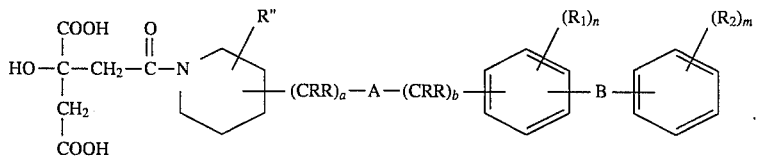
6. A compound according to claim 4 of the formula:
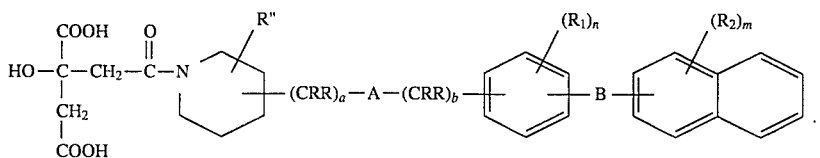
7. A compound according to claim 4 of the formula:
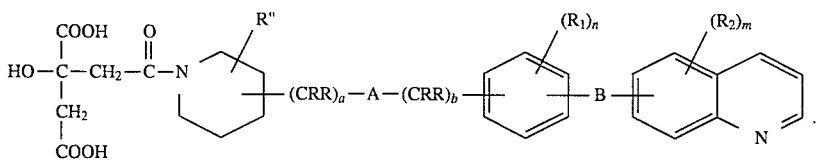
8. A compound according to claim 4 of the formula:

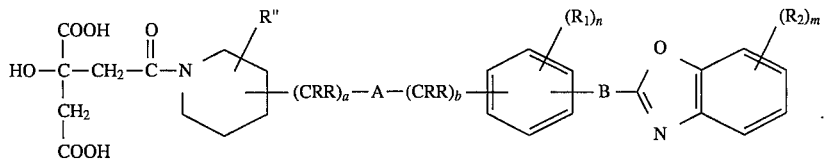

9. A compound according to claim 4 of the formula:

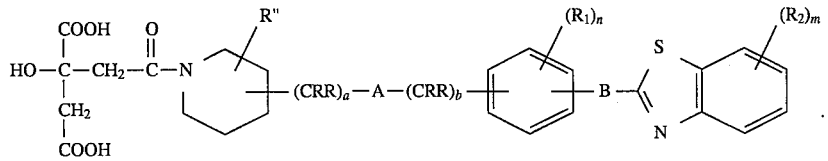

10. A compound according to claim 5 which is 4-[3-hydroxy-2-(3-methoxybiphenyl-4-yl)piperidin-1-ylcarbonyl]-3-hydroxy-3-carboxybutanoic acid or a pharmaceutically acceptable salt thereof.

11. A compound according to claim 6 which is 4-[3-hydroxy-3-(4-naphthalen-2-ylphenyl)piperidin-1-ylcarbonyl]-3-hydroxy-3-carboxybutanoic acid or a pharmaceutically acceptable salt thereof.

12. A compound according to claim 8 which is 4-[3-(4-(benzoxazol-2-yl)benzyloxymethyl)piperidin-1-ylcarbonyl]-3-hydroxy-3-carboxybutanoic acid or a pharmaceutically acceptable salt thereof.

13. A compound according to claim 7 which is 4-{3-hydroxy-3-[4-(2-methoxyquinolin-6-yl)phenyl]piperidin-1-ylcarbonyl}-3-hydroxy-3-carboxybutanoic acid or a pharmaceutically acceptable salt thereof.

14. A method of lowering or maintaining reduced cholesterol levels in a patient requiring such treatment which comprises administering to such patient a squalene synthase inhibitor effective amount of a compound of the formula according to claim 1.

15. A method for inhibiting cholesterol biosynthesis which comprises administering to a patient in need of such inhibition a squalene synthase inhibiting effective amount of a compound according to claim 1.

16. A method according to claim 15 where the patient is in need of a hypocholesterolemic or hypolipidemic agent.

17. A method according to claim 16 for treating atherosclerosis.

18. A pharmaceutical composition comprising a squalene synthase inhibitor effective amount of a compound according to claim 1 in admixture with a pharmaceutical carrier.

19. A pharmaceutical composition according to claim 18 which further includes an HMG CoA reductase inhibitor.

* * * * *